United States Patent [19]

Perlman

[11] Patent Number: 5,149,408
[45] Date of Patent: Sep. 22, 1992

[54] CAPILLARY BLOTTING PAD FOR MOLECULAR TRANSFER TO MEMBRANES

[75] Inventor: Daniel Perlman, Arlington, Mass.

[73] Assignee: Brandeis University, Waltham, Mass.

[21] Appl. No.: 692,579

[22] Filed: Apr. 29, 1991

[51] Int. Cl.$^5$ .......................... C25B 1/00; B01D 57/02
[52] U.S. Cl. .............................. 204/182.3; 204/180.1; 210/679; 210/681
[58] Field of Search ............ 204/299 R, 180.1, 182.3; 210/679, 681

[56] References Cited

U.S. PATENT DOCUMENTS 4,994,166 2/1991 Fernwood ..................... 204/299 R

OTHER PUBLICATIONS

Southern, "Detection of Specific Sequences Among DNA Fragments Separated by Gel Electrophoreus", J. Mol. Biol. (1975) 98, 503–517.

Primary Examiner—John Niebling
Assistant Examiner—Caroline Koestner
Attorney, Agent, or Firm—Lyon & Lyon

[57] ABSTRACT

A capillary blotting sandwich for transferring soluble macromolecules in a liquid medium from a liquid-permeable matrix to a semi-permeable receiving membrane. The blotting sandwich includes: (i) a liquid-permeable matrix layer comprising soluble macromolecules, said matrix having at least one flat surface, (ii) a semi-permeable membrane sheet layer disposed on said flat surface; (iii) an interlocked hydrophilic absorbent fiber-containing material in the form of a non-woven absorbent felt sheet or pad layer disposed on said semi-permeable membrane, wherein said felt layer facilitates capillary transport of a solution through said membrane, whereby said soluble macromolecules in said matrix layer are caused to migrate to said membrane layer.

18 Claims, 1 Drawing Sheet

CAPILLARY BLOTTING PAD FOR MOLECULAR TRANSFER TO MEMBRANES

BACKGROUND OF THE INVENTION

This invention relates to an apparatus and method for capillary transfer of macromolecules to a membrane.

The fractionation and analysis of biochemical macromolecules including DNA, RNA and protein molecules is often assisted by a technique known as slab gel electrophoresis. This technique involves the use of an electric field to induce the migration and separation of different molecular species in aqueous buffered gels. Such electrophoretic gels are most often formed using electrically neutral polymers including agarose and polyacrylamide. Agarose gels are cast from reversible thermosetting sols whereas polyacrylamide gels are typically polymerized and cross-linked in place and are not thermally reversible. Following electrophoretic fractionation of macromolecules in a slab gel, it is often useful, for purposes of analysis, to transfer the macromolecules from the flat gel (approximately 0.1-1.0 cm thick) onto a thin juxtaposed membrane (typically consisting of microporous nitrocellulose or nylon material). The process of transferring macromolecules such as DNA from a slab gel to a microporous membrane usually involves a capillary blotting procedure in which a salt-containing buffer (e.g., 1.5M NaCl, 0.15M Tris buffer) is fed to the underside of the slab gel. Capillary transport of the buffer solution carries the macromolecules from the gel, upward to the overlayed microporous receiving membrane where the macromolecules are captured. A carefully positioned and weighted stack of absorbent paper is placed on top of the membrane to provide liquid wicking action allowing a substantial volume of buffer to move uniformly upward through the blotting sandwich containing the gel, membrane, and stack of absorbent paper. Air bubbles in the structure must be avoided since any which are accidentally trapped in the blotting sandwich, above or below the slab gel, tend to locally block capillary transport of buffer, compromising the fidelity and quality of the resulting molecular blot. Maniatis et al. in *Molecular Cloning: A Laboratory Manual* (Cold Spring Harbor Laboratory, N.Y.) provide a detailed description and protocol describing the molecular blotting procedure. A diagram from this prior art reference is provided in the Figure as illustrative of the method. When this blotting procedure is applied to the transfer of DNA molecules from a gel, it is known as Southern blotting. When the procedure is used for RNA and protein molecules it is known as northern and western blotting respectively.

Absorbent materials utilized in capillary blotting pads for transfer of macromolecules to microporous membranes include paper towels, filter paper sheets and paper pads.

SUMMARY OF THE INVENTION

In general, the present invention is directed toward improving the macromolecular capillary blotting procedure by providing a functionally superior absorbent material whose structure and composition provides improved wicking action in the transfer process. The invention is also designed to reduce physical pressure on, and distortion of the gel, as well as the probability that air bubbles will become trapped in the absorbent blotting material and interfere with the capillary transfer of macromolecules. For example, the prior art procedure (Maniatis et al., supra) which employs paper absorbent sheets or pads, requires that approximately a 500 g weight be placed on top of the stack of paper to eliminate air spaces. In contrast, the absorbent material used in the present invention is much softer and compliant, allowing a substantially smaller weight to accomplish the same task. The smaller weight, by compressing the absorbent material and underlying gel to a lesser extent, allows greater absorption of liquid in the material while reducing physical distortion of the soft gel.

The limitations of absorbent paper in molecular blotting operations are largely overcome by the use of non-woven textile fiber pads (hereinafter termed felt pads) comprising from 25% to 100% by weight hydrophilic absorbent textile fiber material and between 0% and 75% by weight support fiber. The hydrophilic fiber is of either natural or synthetic origin. Unlike absorbent paper and filter paper pad and sheet products which tend to be dense and relatively hard because they are usually formed from short wood and/or cotton-derived fibers which are deposited in an aqueous environment, felt pads are softer and relatively compliant, being formed by the interlocking of long fibers by a non-woven textile process carried out in the normal air environment. The difference in fiber lengths and methods of production results in the felt pads used in the present invention typically having only 10-50% the weight density, (i.e., grams per cubic centimeter), that is characteristic of paper products. More typically, the felt pads possess only 10-25% the weight density of typical paper products. This low density leaves more space in the material for absorption of liquid. Preferably the felt pads of the present invention have a density of between 0.05 and 0.25 g/cm$^3$. For example, a typical 100% rayon felt pad (manufactured by the National Felt Company, Easthampton, MA) and useful in the present invention has a density of between 0.05 and 0.10 g/cm$^3$ which may be compared to 100% cotton paper pad products (e.g., Ahlstrom Filtration, Inc. Mt. Holly Spring, PA) having a density of approximately 0.3 g/cm$^3$. While both pads acquire a density of approximately 1.0 when saturated with aqueous solution, a paper pad of density 0.3 g/cm$^3$ absorbs approximately 3-4 times its weight of liquid while a rayon felt pad absorbs over 10 times its weight of liquid. This economic use of material offers a substantial cost-savings to the consumer. Typically, the felt absorbent pads of the present invention absorb 10-15 times their weight of aqueous salts buffer and sometimes as much as 25 times their weight.

One class of felt pads preferred for use in the present invention is formed using a continuous needle punching process which causes the long-fibers such as rayon, to become entangled and interlocked in a random non-woven array. Unlike water-deposited absorbent paper fibers which tend to disaggregate in water causing paper disintegration (if thorough soaking or washing is attempted), felt pads useful in the present invention remain coherent and intact during aqueous soaking, rinsing and gentle washing. Thus, felt pads may be washed free of salts and other contaminants following the blotting operation, and subsequently may be dried and reused. The felt material reaquires a textile-like softness and compliant structure which permits stacking and good physical contact between multiple felt pads. This good contact is necessary for subsequent capillary transport of liquid during blotting. Paper pads, in contrast, even if successfully washed (by careful suction filtration, for example), typically warp or curl during drying thus preventing reuse as a capillary blotting pad.

One of the problems associated with the use of paper sheets and pads in the capillary blotting procedure is the tendency of air bubbles to become trapped between the paper layers which are in the process of becoming saturated with buffer. Such bubbles, which may form as buffer rises through absorbent sheets of paper, tend to change the flow of the buffer resulting in poor fidelity of macromolecular transfer to the microporous membrane used to capture the molecules.

A significant advantage found in the use of hydrophilic felt pads is their relative immunity to trapping of air bubbles. In fact, the open fiber macropermeable structure of felt pads allows air bubbles to rise through the felt fiber structure. Furthermore, the softer, more permeable, and more compliant structure of the felt pads compared to compressed filter pads, allows more rapid and convenient stacking of the pads to form the structure shown in the Figure. Also, the amount of weight placed on the absorbent material to eliminate air spaces trapped in the blotting sandwich is substantially less with the felt pads than the paper absorbent. For example a 100-150 g weight is sufficient for a stack of 5"×5" felt pads approximately 1-3 inches thick whereas approximately 500 g is required for a stack of absorbent paper towels of comparable thickness. Hydrophilic felt pads each ranging in thickness from approximately 1/32-2 inches thick have been successfully stacked to form absorbent decks ranging from about 1/2 to 6 inches tall, allowing capillary blot-transfer of many different species of macromolecules.

Thus, in a first aspect, the invention features the use of a capillary blotting sandwich for transferring macromolecules in a liquid medium from a liquid-permeable matrix material to a semi-permeable receiving membrane. The capillary blotting sandwich includes a liquid-permeable matrix layer comprising soluble macromolecules. This matrix, e.g., an electrophoretic slab gel, has at least one flat surface. A semi-permeable membrane sheet layer is disposed on this surface. In turn, an interlocked hydrophilic absorbent fiber-containing material in the form of a non-woven absorbent felt sheet or pad layer is disposed on the semi-permeable membrane. The absorbent felt layer facilitates capillary transport of a solution through the semi-permeable membrane, whereby the soluble macromolecules originally in the liquid-permeable matrix layer are caused to migrate to the membrane layer.

In a related aspect, the invention features a method for transferring macromolecules in a liquid solution medium from a flat liquid-permeable matrix layer to a semi-permeable receiving membrane layer including the steps of providing a two-sided semi-permeable membrane layer adapted to transmit liquid solutions by capillary transport and resist passage of macromolecules, and also providing an interlocked hydrophilic absorbent material in the form of a non-woven absorbent felt sheet or pad layer. The liquid-permeable matrix layer is placed in contact with one side of the membrane layer and the absorbent felt layer is placed in contact with the other side of the membrane layer. Capillary transport of the liquid solution from the liquid-permeable matrix layer toward the absorbent layer is then initiated. The sandwiched layers of matrix, membrane and absorbent are allowed to remain in contact for sufficient time for the macromolecules in the matrix to be transferred toward the membrane.

In preferred embodiments, the liquid medium and the liquid-permeable matrix of the capillary blotting sandwich are an aqueous medium and an aqueous-permeable matrix. The absorbent felt sheet or pad comprises between 25% and 100% by weight hydrophilic absorbent fiber and between 0% and 75% by weight support fiber, the felt layer has a density between 0.05 and 0.25 g/cm$^3$ and is between 1/32 and 2 inches thick; the absorbent fiber material in the felt sheet or pad is either a natural or synthetic absorbent material including cotton, rayon, acrylic fibers, polyisobutylene copolymer fibers and polyacrylate superabsorbent materials; the support fiber in the felt sheet or pad is, for example, polyester, nylon, dacron, polyethylene or polypropylene; the felt layer is also stable when soaked in an aqueous liquid and subject to frictional forces; thus it is washable and reusable. The felt layer is capable of absorbing as much as 25 times its weight of aqueous salts buffer in the course of the blotting procedure, most typically between 10 and 15 times its weight of the aqueous salts buffer. For maximum effectiveness the felt layer is sufficiently permeable and compliant whereby the amount of weight to be placed on this felt layer to eliminate air spaces trapped in the blotting sandwich is substantially reduced compared to paper absorbents. The type of liquid-permeable matrix layer used in the blotting sandwich of the present invention is usually an electrophoretic matrix but may also be a chromatographic matrix, e.g., paper chromatography sheets. Most often the matrix layer is an electrophoretic slab gel; the slab is generally cast from agarose or acrylamide polymer materials which form gels. A hydrophilic wick material such as a filter paper sheet may be also added to the blotting sandwich of the present invention. This wick is placed in contact with the liquid-permeable matrix layer and an external liquid solution reservoir (such as a salt-buffer reservoir) which provides additional solution to assist in the capillary transport of the macromolecules from the matrix to the semi-permeable membrane which captures the macromolecules.

DESCRIPTION OF THE PREFERRED EMBODIMENT

Figure 1:
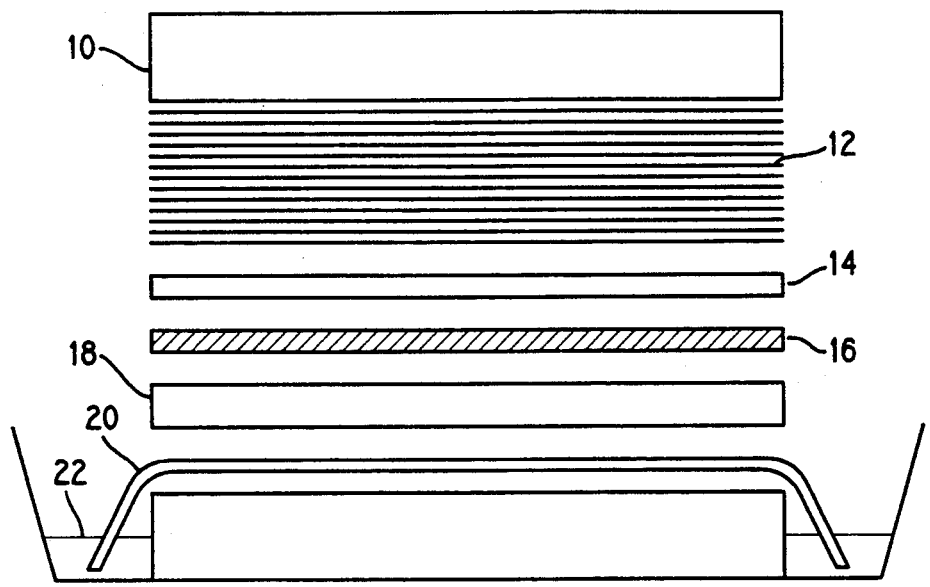
FIG. 1 represents the most common prior art system for transfer of DNA from agarose gels to nitrocellulose filter paper.
Figure 2:
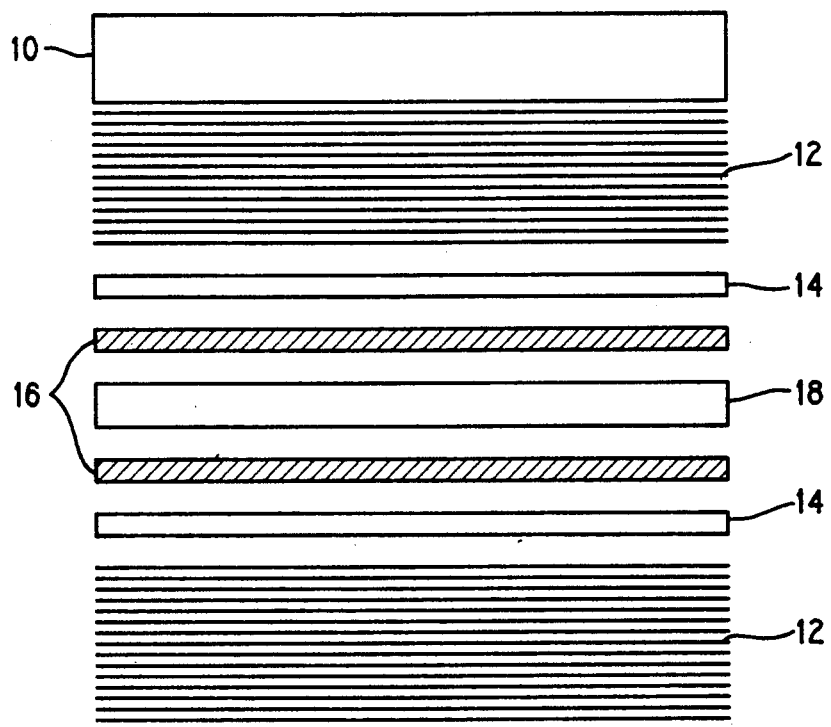
FIG. 2 represents one embodiment of the instant invention wherein duplicate nitrocellulose filters from a single gel are prepared. The transfer buffer is supplied only by the liquid in the agarose gel itself.

The drawing is a representation of a prior art method of transferring DNA from an agarose gel to a nitrocellulose membrane. In the figure, 10 represents a weight; 12 represents paper towels; 14 represents filter paper; 16 represents a nitrocellulose membrane; 18 represents a gel matrix; 20 represents a filter paper wick; and 22 represents a buffer reservoir.

The present invention utilizes a capillary absorbent blotting sheet or pad in the transfer of macromolecules to semi-permeable membranes. The blotting pad is manufactured using hydrophilic textile fibers which are entangled and interlocked in a non-woven process, such as by a continuous needle punching process, commonly used to form felt cloth-type materials. Felt materials can subsequently absorb liquid and aqueous salt solutions by capillary transport and can sequester and transfer the liquid upward through multiple layers of the felt. Compared with absorbent paper towels and paper filter pads, the felt material preferred for the present use is about 5-fold lighter, i.e., it has a density of 0.05 g/cm$^3$ compared to 0.3 g/cm$^3$ for paper. The preferred density range of the material is between 0.05 and 0.25 g/cm$^3$. Felt material chosen for the present use is also soft and compliant, alleviating the need for any substantial weight being applied to the absorbent sheets to establish wicking, i.e., capillary transmission of liquid. Furthermore, the felt material is preferably washable so that salts may be removed and the sheet reused following drying. Absorbent felt pads of almost any thickness may be used as long as their surfaces are sufficiently flat and the pads sufficiently uniform in density to assure consistent capillary absorption and continuity with each underlying layer. Pads ranging in thickness from 1/32" to 2" have been successfully used. The mix ratio of hydrophilic to hydrophobic fibers in the felt pad significantly influences the ability of the pad to hold aqueous liquid and transmit the liquid to upper layers of the material. Thus, at least 25% of the fiber material by weight should be both hydrophilic and absorbent in nature while no than 75% of the fiber should be hydrophobic. The latter fiber serves as a support fiber matrix and reduces the tendency of the absorbent fiber material to collapse on itself when saturated. For example, cotton fiber when present without a support fiber, tends to collapse while rayon, a preferred fiber for use in the present felt pads can often be used without a support fiber. Rayon pads (100% by weight rayon) have been shown to possess excellent liquid retention, absorbing as much as fifteen times their weight of aqueous buffer solution. Furthermore, the rayon material exhibits excellent capillary transmission of aqueous solutions as well as sufficient durability required for washing, drying and reuse of the pads.

A preferred fiber material used to form the hydrophilic felt pads of the present invention is 100% rayon fiber. A medical grade of rayon fiber softened and lubricated with trace concentrations of a non-ionic surfactant such as polyethylene glycol or polysorbate has been used in a continuous needle punching felt forming process, National Felt Company, Inc., to produce useful and easily wettable blotting pads. Alternatively the rayon fiber has been mixed with 25-75% by weight polyester, nylon, dacron, polyethylene or polypropylene fibers which, by their waterproof nature, constitute an inert support fiber which helps prevent any compaction of the rayon pad when wet. Both natural and synthetic hydrophilic fibers have been used as the absorbent component in the sheets and pads of the present invention. For example, cotton fiber has been used in place of rayon for absorbency in the felt structure. A "super-absorbent" fiber known as Fibersorb SA-7000 (a polyisobutylene copolymer fiber manufactured by ARCO Chemical Company) has also been used in a blended fiber mixture with polyester fiber to provide felt pads with even greater absorption capacities for aqueous solutions. Polyacrylate superabsorbent has been used as well. For example, a blend of 25-50% by weight Fibersorb SA-7000 and polyester fibers has been used by the National Felt Company to manufacture absorbent sheets.

Other examples of hydrophilic fiber materials useful in the present invention include the polyisobutylene fiber, Fibersorb SA-7000, polyacrylate superabsorbent fiber, and regular cotton and acrylic textile fibers. Examples of hydrophobic support fibers which may be mixed with the absorbent fibers, include polyester, nylon, dacron, polyethylene and polypropylene.

Macromolecular transfer blotting, may also involve the transport of chromatogram-fractionated molecules from permeable chromatographic matrix materials such as cellulosic chromatography paper to semi-permeable membranes (such as nylon and nitrocellulose membranes) using the same technique as for gels.

The following is one example of employing felt pads in the capillary blotting and transfer of macromolecules to semi-permeable membrane. This example is not limiting in the invention which is limited only by the scope of the claims.

EXAMPLE

An aqueous electrophoretic slab gel (measuring 15 cm × 15 cm × 7 mm thick) containing 1% (w/v) agarose was cast according to standard procedures (Maniatis et al., supra). The gel was loaded with a set of double-standard marker DNA fragments and was subjected to electrophoresis to separate the fragments (ranging in size from 100 base pairs to 15,000 base pairs). Subsequently the slab gel was stained with ethidium bromide (1 ug/ml) and was transferred to a flat platform covered by Whatman 3 MM paper which extended into the surrounding reservoir of DNA transfer buffer (buffered 3M sodium chloride). A buffer-saturated semi-permeable membrane (nitrocellulose, 0.45 micron pore size, Millipore Corporation) was placed on top of the gel, followed by two sheets of Whatman 3 MM paper and ten sheets of absorbent 100% rayon felt (each sheet measuring 3/32 inch thick and weighing 4 oz. per yd$^2$). A flat plastic sheet weighing approximately 100 g was placed on top of the gel transfer sandwich described above to assure physical contact between all the layers. After approximately twelve hours, the sandwich was disassembled and, based upon the absence of DNA in the agarose gel, the DNA transfer was judged to be complete. Examination of the ethidium bromide-stained DNA bands on the nitrocellulose membrane showed excellent uniformity and fidelity of DNA band transfer. Following the procedure, the rayon felt pads were soaked in distilled water, rinsed five times in distilled water, and dried in a warming oven at approximately 90° C. The rayon pads were reused several times before discarding.

Other embodiments are within the following claims.

I claim:

1. A method for transferring macromolecules in a liquid solution medium from a flat liquid-permeable matrix layer to a semi-permeable receiving membrane layer comprising the steps of:

providing a two sided semi-permeable membrane layer adapted to transmit liquid solutions by capillary transport and resist passage of macromolecules, providing an interlocked hydrophilic absorbent-containing material in the form of a non-woven absorbent felt layer comprising from 25% to 100% by weight hydrophilic absorbent textile fiber material, placing said liquid-permeable matrix layer is contact with one side of said membrane layer placing said absorbent felt layer in contact with the other side of said membrane layer, initiating capillary transport of liquid solution from said liquid-permeable matrix layer toward said absorbent layer, and allowing the resulting sandwiched layers of said matrix, membrane and absorbent to remain in contact for sufficient time so that said macromolecules are transferred from said matrix toward said membrane.

2. The method of claim 1 wherein said liquid solution is an aqueous medium and said matrix is an aqueous-permeable matrix.

3. The method of claim 1 wherein said felt layer comprises between 25% and 100% by weight hydrophilic absorbent fiber and between 0% and 75% by weight support fiber.

4. The method of claim 1 wherein said felt layer has a density of between 0.05 and 0.25 g/cm$^3$.

5. The method of claim 1 wherein said felt layer is between 1/32 and 2 inches thick.

6. The method of claim 1 wherein said absorbent fiber is selected from the group of natural and synthetic absorbent fiber materials.

7. The method of claim 6 wherein said fiber material are selected from the group consisting of cotton, rayon, acrylic fibers, polyisobutylene copolymer fibers, and polyacrylate superabsorbent materials.

8. The method of claim 3 wherein said support fiber is selected from the group consisting of polyester, nylon, dacron, polyethylene and polypropylene.

9. The method of claim 1 wherein said felt layer is stable when soaked in an aqueous liquid and subject to frictional forces.

10. The method of claim 1 wherein said felt layer is capable of absorbing as much as 25 times its weight of aqueous salts buffer.

11. The method of claim 1 wherein said felt layer is capable of absorbing between approximately 10 and 15 times it weight of aqueous salts buffer.

12. The method of claim 1 wherein said absorbent felt layer is sufficiently permeable, and compliant, whereby the amount of weight to be placed on said layer to eliminate air spaces trapped in a blotting sandwich is substantially reduced compared to paper absorbents.

13. The method of claim 1 wherein said matrix layer contains macromolecules, and is chosen from an electrophoretic matrix and a chromatographic matrix.

14. The method of claim 13 wherein said electrophoretic matrix is an electrophoretic slab gel.

15. The method of claim 14 wherein said slab gel is chosen from agarose and acrylamide gels.

16. The method of claim 1 further comprising placing a hydrophilic wick in contact with said liquid-permeable matrix layer and an external aqueous solution reservoir, whereby said reservoir provides aqueous solution to assist in the capillary transport of said macromolecules from said matrix to said membrane.

17. The method of claim 1 wherein said liquid is aqueous.

18. The method of claim 1 wherein prior to a said placing step, a hydrophilic wick is placed in contact with said liquid-permeable matrix layer and an external solution reservoir, whereby said reservoir provides solution to assist in the capillary transport of said macromolecules from said matrix to said membrane.

* * * * *